United States Patent
Katoh et al.

(10) Patent No.: US 9,255,123 B2
(45) Date of Patent: Feb. 9, 2016

(54) SKIN-BEAUTIFYING AGENT

(75) Inventors: Ken Katoh, Hokkaido (JP); Hiroshi Ueno, Hokkaido (JP); Yuko Ono, Hokkaido (JP); Noriko Ueda, Hokkaido (JP)

(73) Assignee: MEGMILK SNOW BRAND CO., LTD., Hokkaido (JP)

(*) Notice: Subject to any disclaimer, the term of this patent is extended or adjusted under 35 U.S.C. 154(b) by 0 days.

(21) Appl. No.: 14/001,964

(22) PCT Filed: Mar. 7, 2012

(86) PCT No.: PCT/JP2012/055811
§ 371 (c)(1),
(2), (4) Date: Aug. 28, 2013

(87) PCT Pub. No.: WO2012/121286
PCT Pub. Date: Sep. 13, 2012

(65) Prior Publication Data
US 2013/0338336 A1 Dec. 19, 2013

(30) Foreign Application Priority Data
Mar. 10, 2011 (JP) .................. 2011-053276

(51) Int. Cl.
C07K 2/00 (2006.01)
A61K 35/20 (2006.01)
A61Q 19/00 (2006.01)
C07K 4/10 (2006.01)
A23L 1/305 (2006.01)
A61K 38/01 (2006.01)
A23K 1/16 (2006.01)
A23K 1/18 (2006.01)
A61K 8/64 (2006.01)
A61Q 19/08 (2006.01)

(52) U.S. Cl.
CPC ............... *C07K 4/10* (2013.01); *A23K 1/1631* (2013.01); *A23K 1/1634* (2013.01); *A23K 1/1846* (2013.01); *A23K 1/1866* (2013.01); *A23L 1/3053* (2013.01); *A23L 1/3056* (2013.01); *A61K 8/64* (2013.01); *A61K 38/018* (2013.01); *A61Q 19/007* (2013.01); *A61Q 19/08* (2013.01); *A23V 2002/00* (2013.01)

(58) Field of Classification Search
CPC .. A23L 1/3053; A23L 1/3056; A23K 1/1846; A23K 1/1634; A23K 1/1631; A23K 1/1866; A23V 2002/00; A23V 2200/318; A23V 2250/54252; A61K 38/018; A61K 8/64; A61Q 19/08; A61Q 19/007; C07K 4/10
See application file for complete search history.

(56) References Cited

U.S. PATENT DOCUMENTS

| 4,463,017 | A | 7/1984 | Hidalgo et al. |
| 5,039,532 | A | 8/1991 | Jost et al. |
| 5,314,873 | A * | 5/1994 | Tomita et al. ............... 514/18.8 |
| 5,952,193 | A | 9/1999 | Shimamura et al. |
| 6,506,732 | B1 | 1/2003 | Amiot |
| 2006/0247162 | A1 | 11/2006 | Morita et al. |
| 2008/0063674 | A1 | 3/2008 | Vollhardt et al. |
| 2010/0035819 | A1 | 2/2010 | Morita et al. |
| 2010/0135941 | A1 | 6/2010 | Watanabe et al. |
| 2010/0273718 | A1 | 10/2010 | Kumar et al. |
| 2013/0225497 | A1 | 8/2013 | Kato et al. |
| 2013/0225501 | A1 | 8/2013 | Kato et al. |
| 2013/0310318 | A1 | 11/2013 | Ueno et al. |

FOREIGN PATENT DOCUMENTS

| CN | 1771051 | 5/2006 |
| CN | 1976676 | 6/2007 |
| CN | 101616657 | 12/2009 |
| EP | 2 138 159 | 12/2009 |
| GB | 2 046 591 | 11/1980 |
| JP | 2-2319 A | 1/1990 |
| JP | 2-138991 A | 5/1990 |
| JP | 4-112753 A | 4/1992 |
| JP | 8-98656 A | 4/1996 |
| JP | 9-30928 A | 2/1997 |
| JP | 2002-161031 A | 6/2002 |
| JP | 2003-144095 | 5/2003 |
| JP | 2007-246413 | 9/2007 |

(Continued)

OTHER PUBLICATIONS

Whey protein hydrolysate, from http://www.bodybuilding.com/fun/muscle-up-the-smart-whey-expert-guide-whey-protein-h . . . , pp. 1-10, accessed May 6, 2014.*

(Continued)

*Primary Examiner* — Julie Ha
*Assistant Examiner* — Li Ni Komatsu
(74) *Attorney, Agent, or Firm* — Greenblum & Bernstein, P.L.C.

(57) ABSTRACT

The invention addresses the problem of providing a skin-beautifying agent with beautifying effects such as skin moisturizing, skin beautification, prevention of rough skin, wrinkle prevention, prevention of reduced elasticity, etc., and a skin-beautifying product such as a cosmetic, food or drink, feed, medicine, etc. that contains said skin-beautifying agent. The skin-beautifying agent is characterized in containing a hydrolyzate of whey protein as an active ingredient. Using a whey protein hydrolyzate having the characteristics of a molecular weight distribution of 10 kDa or less, a main peak of 200 Da-3 kDa, APL (average peptide length) of 2-8, free amino acid content of 20% or less, and a β-lactoglobulin antigenicity of $1/10,000$ or less, in particular, provides a skin-beautifying agent of low allergenicity and low bitterness.

7 Claims, No Drawings

(56) References Cited

FOREIGN PATENT DOCUMENTS

| WO | 2004/098632 A1 | 11/2004 |
|---|---|---|
| WO | 2006/000350 | 1/2006 |
| WO | 2008/088472 | 7/2008 |
| WO | 2008/111562 A1 | 9/2008 |

OTHER PUBLICATIONS

Water, from http://www.biology-online.org/dictionary/Water, pp. 1-3, accessed Apr. 24, 2014.*
Glycerol, from http://www.naturalwellbeing.com/learning-center/Glycerol, pp. 1-3, accessed Apr. 24, 2014.*
Effects of Aging on the Skin, from http://www.merckmanuals.com/home/print/skin_disorders/biology_of_the_skin/effects_of . . . , page 1, accessed Apr. 9, 2012.*
Dry skin-Signs and symptoms, from https://www.aad.org/dermatology-a-to-z/diseases-and-treatments/a---d/dry-skin/signs-symptoms, p. 1, accessed Apr. 17, 2015.*
English translation of JP 04-112753 A, pp. 1-16, accessed Apr. 2015.*
Wang et al., "Whey peptides improve wound healing following caesarean section in rats", British Journal of Nutrition, vol. 104, pp. 1621-1627, 2010.
Shimizu et al., "Dietary Whey Protein Hydrolysate Suppresses Development of Atopic Dermatitis-like Skin Lesions Induced by Mite Antigen in NC/Nga Mice", Allergology International, vol. 55, No. 2, pp. 185-189, 2006.
U.S. Appl. No. 13/981,698 to Ken Katoh et al., filed Jul. 25, 2013.
International Search Report for PCT/JP2012/055811, mailed May 22, 2012.
International Preliminary Report on Patentability for PCT/JP2012/055811, mailed Sep. 19, 2013.
Guadix et al., "Production of whey protein hydrolysates with reduced allergenicity in a stable membrane reactor", *Journal of Food Engineering,* vol. 72, pp. 398-405, 2006.
Extended European Search Report for EP Patent Application No. 12754831 1, mailed Sep. 19, 2014.

* cited by examiner

SKIN-BEAUTIFYING AGENT

The instant application is the National Stage of International Application No. PCT/JP2012/055811, filed Mar. 7, 2012, which application claims priority to Japanese Patent Application No. 2011-053276, filed Mar. 10, 2011.

TECHNICAL FIELD

The invention relates to a skin-beautifying agent that exhibits excellent a skin-beautifying effect, is effective for moisturizing, beautifying skin, preventing rough skin, preventing skin wrinkles, and preventing loss of elasticity in skin, has low bitterness, and is excellent in stability and safety.

The invention also relates to a skin-beautifying cosmetic, a skin-beautifying food or drink, a skin-beautifying nutrient composition, a skin-beautifying feed, and a skin-beautifying drug including the skin-beautifying agent.

BACKGROUND ART

Skin is an interface between a living body and the external environment, and has a skin barrier function that prevents water loss from the body, and prevents penetration of biologically harmful substances, such as microorganisms, allergens and the like from the external environment. Keratin intercellular lipids, mainly ceramide, sebum and the like in the stratum corneum act as these skin barrier function. The stratum corneum must have a water content of 10 to 20% in order to achieve a normal function and maintain a healthy condition. Therefore, softness and the elasticity of skin are maintained by water retained in the stratum corneum due to the skin bather function. When the water content decreases in the stratum corneum, skin loses its softness and becomes hard, thereby cracks and the like may occur. So-called chapped skin of which patterns are invisible or unclear shows a significant decrease in water content in the stratum corneum. Rough skin not only has poor cosmetic appearance, but also is a preliminary stage to cause skin disease, and rough skin has a pathological significance. Further, by improving rough skin conditions, the surface of dry and flaky skin can be smoothed, thereby leading to improvement of fine wrinkles. It has been known that when the skin barrier function of the stratum corneum has deteriorated, water loss from skin is significant in comparison with healthy condition, that is, increased transepidermal water loss (TEWL) is observed. The TEWL is closely related with the barrier function and the moisturizing function of the stratum corneum, and is used as an index of the skin barrier function. Therefore, skin can be maintained in a healthy condition i.e., beautiful condition by increasing the water content in skin, or reducing the TEWL, or suppressing an increase in TEWL.

In recent years, studies on the mechanism of skin have been carried out, and it has been confirmed that macroscopic causes of dry feeling of the skin and rough skin are complexly involved in the effects of sunlight (ultraviolet rays), drying, oxidization, and the like in addition to effects due to decrement of the metabolism with aging. It has been found that these effects caused by such factors significantly decrease the amount of collagen fibers that are the main matrix component of the dermis. When a mechanism to keep tension and elasticity of skin that is maintained by the collagen fibers is destroyed by the effects of ultraviolet rays and the like, wrinkles or slacks of the skin increase. Since collagen molecules can retain water, and thus maintain skin in a moisturized condition, skin becomes dry and rough when collagen is destroyed due to external factors. Therefore, wrinkles and slacks of skin can be prevented by promoting biosynthesis of collagen that is one of the main components of the dermis layer, and skin can be maintained in a healthy condition, that is, beautiful skin condition. In recent years, deterioration in the skin condition of animals, particularly pets, due to allergy and the like has become a major issue. The skin condition of animals can be improved by moisturizing and caring the skin, healthy skin condition can be maintained.

A milk protein hydrolysate has been used for various commercial products in order to prevent food allergy caused by cow milk or dairy products. In particular, it has been considered that a whey protein of cow milk functions as an allergen, differing from a protein in mother's milk. Therefore, it has been known that a whey protein has been hydrolyzed using a protease in order to prevent this problem (see Patent Documents 1 to 3). It has been also known that a whey protein hydrolysate suppresses the progress of atopic dermatitis (see Non-patent Document 1), and improves curing wound after Cesarean section (see Non-patent Document 2).

PRIOR ART DOCUMENT

Patent Document

Patent Document 1: JP-A-H02-002319
Patent Document 2: JP-A-H02-138991
Patent Document 3: JP-A-H04-112753

Non-Patent Document

Non-patent Document 1: Allergology International. 2006; 55: 185-189
Non-patent Document 2: British Journal of Nutrition 2010; August 9: 1-7

SUMMARY OF THE INVENTION

Problems to be Solved by the Invention

An object of the invention is to provide a skin-beautifying agent that exhibits excellent beauty effects, such as excellent skin-moisturizing, skin-protecting, preventing or improving rough skin, preventing wrinkles, preventing loss of elasticity in skin, or the like. Another object of the invention is to provide a skin-beautifying cosmetic, a skin-beautifying food or drink, a skin-beautifying nutrient composition, a skin-beautifying feed, or a skin-beautifying drug that includes a skin-beautifying agent that exhibits excellent beauty effects, such as excellent skin-moisturizing, skin-protecting, preventing or improving rough skin, preventing wrinkles, preventing loss of elasticity in skin, or the like.

Means for Solving the Problems

The inventors of the invention conducted extensive studies in order to achieve the above objects, and found that a whey protein hydrolysate has a skin-beautifying effect.

Specifically, the invention includes the followings.

(1) A skin-beautifying agent including a whey protein hydrolysate as an active ingredient.

(2) The skin-beautifying agent according to (1), wherein the whey protein hydrolysate has a hydrolysis rate of 25% or more.

(3) The skin-beautifying agent according to (1) or (2), wherein the whey protein hydrolysate has following characteristics (A) to (D);

(A) the molecular weight thereof is 10 kDa or less and the main molecular weight peak thereof is 200 Da to 3 kDa, (B) the average peptide length (APL) thereof is 2 to 8, (C) the free amino acid content hereof is 20% or less, and (D) the antigenicity thereof is equal to or less than 1/10,000th of that of β-lactoglobulin.

(4) The skin-beautifying agent according to any one of (1) to (3), wherein the whey protein hydrolysate is obtained by hydrolyzing a whey protein using a heat-resistant protease at pH 6 to 10 and 50 to 70° C. while thermally denaturing the whey protein, and inactivating the protease by heating.

(5) The skin-beautifying agent according to any one of (1) to (3), wherein the whey protein hydrolysate is obtained by hydrolyzing a whey protein using a protease at pH 6 to 10 and 20 to 55° C., heating the resultants to 50 to 70° C., further hydrolyzing the unhydrolyzed whey protein using a heat-resistant protease at pH 6 to 10 and 50 to 70° C. while thermally denaturing, and inactivating the protease by heating.

(6) A skin-beautifying cosmetic, a skin-beautifying food or drink, a skin-beautifying nutrient composition, a skin-beautifying feed, or a skin-beautifying drug including the skin-beautifying agent according to any one of (1) to (5).

(7) A method for moisturizing or protecting mammalian skin, preventing or improving rough skin of mammalian, or preventing wrinkles or decrease in elasticity of mammalian skin, comprising orally or parenterally administering a whey protein hydrolysate.

(8) The method according to (7), wherein the whey protein hydrolysate has following characteristics (A) to (D);

(A) the molecular weight thereof is 10 kDa or less and the main molecular weight peak thereof is 200 Da to 3 kDa, (B) the average peptide length (APL) thereof is 2 to 8, (C) the free amino acid content thereof is 20% or less, and (D) the antigenicity thereof is equal to or less than 1/10,000th of that of β-lactoglobulin.

(9) The method according to (7), wherein the whey protein hydrolysate is obtained by hydrolyzing a whey protein using a heat-resistant protease at pH 6 to 10 and 50 to 70° C. while thermally denaturing the whey protein, and inactivating the protease by heating.

(10) The method according to (7), wherein the whey protein hydrolysate has following characteristics (A) to (E);

(A) the molecular weight thereof is 10 kDa or less and the main molecular weight peak thereof is 200 Da to 3 kDa, (B) the average peptide length (APL) thereof is 2 to 8, (C) the free amino acid content thereof is 20% or less, (D) the antigenicity thereof is equal to or less than 1/10,000th of that of β-lactoglobulin, and (E) the average molecular weight thereof is 300 to 500 Da.

(11) The method according to (7), wherein the whey protein hydrolysate is obtained by hydrolyzing a whey protein using a heat-resistant protease at pH 6 to 10 and 50 to 70° C. while thermally denaturing the whey protein, and inactivating the protease by heating, and then concentrating using an ultrafiltration (UF) membrane and/or a microfiltration (MF) membrane.

Effects of the Invention

The skin-beautifying agent according to the invention exhibits a significant skin-moisturizing effect and a skin collagen production-promoting effect, and may be useful for moisturizing or protecting skin, preventing or improving rough skin, preventing skin wrinkles, and preventing or treating loss of elasticity in skin. Since the skin-beautifying agent according to the invention is produced using a whey protein as a raw material, the skin-beautifying agent can be easily and economically produced.

EMBODIMENTS FOR CARRYING OUT THE INVENTION

A whey protein hydrolysate that is included in a skin-beautifying agent of the invention as an active ingredient may be obtained by the method disclosed in Patent Document 3, for example. According to the method disclosed in Patent Document 3, a whey protein is adjusted to pH of 6 to 10 and a temperature of 50 to 70° C., and a heat-resistant protease is added thereto to hydrolyze while thermally denaturing, and the protease is inactivated by heating, thereby obtaining a whey protein hydrolysate. Note that the yield of the whey protein hydrolysate can be further improved by preliminarily hydrolyzing a whey protein using a protease at pH 6 to 10 and 20 to 55° C. prior to the above hydrolyzation by a heat-resistant protease, and then immediately hydrolyzing the resultant under the above conditions without cooling the resultant. The whey protein hydrolysate prepared as described above may be concentrated using an ultrafiltration (UF) membrane having a molecular weight cut-off of 1 to 20 kDa, preferably 2 to 10 kDa, and/or a microfiltration (MF) membrane having a molecular weight cut-off of 100 to 500 Da, preferably 150 to 300 Da. The bitterness of the whey protein hydrolysate can be reduced while improving the transparency of the whey protein hydrolysate by adjusting the average molecular weight of the whey protein hydrolysate to 300 to 500 Da utilizing the above membrane treatment.

The term "whey protein" used herein refers to whey prepared from milk of a mammal, such as cow, goat, sheep, human or the like, an aggregate, a powder, or a purified product thereof. The whey protein is used in a state of an aqueous solution when hydrolyzing the whey protein using a protease.

When preparing a whey protein hydrolysate according to the method disclosed in Patent Document 3, the whey protein aqueous solution is adjusted to pH 6 to 10. Note that the whey protein aqueous solution need not necessarily be adjusted the pH thereof since a whey protein normally has a pH within the above range. When the whey protein aqueous solution need be adjusted the pH, the whey protein aqueous solution is adjusted to pH 6 to 10 using a solution of an acid, such as hydrochloric acid, citric acid, lactic acid or the like or an alkali, such as caustic soda, calcium hydroxide, sodium phosphate or the like. The whey protein aqueous solution is heated to 50 to 70° C. It is preferable to add the heat-resistant protease before heating the whey protein aqueous solution rather than at the above temperature from the viewpoint of the yield. The optimum temperature for a normal protease is 40° C. or less, and the optimum temperature for a heat-resistant protease is 45° C. or more. Any heat-resistant protease may be used without limitation as long as the protease is known as a heat-resistant protease having such an optimum temperature of 45° C. or more. Examples of such a heat-resistant protease include papain, PROTEASE S (trade name) (enzyme preparation/protease), PROLEATHER (trade name) (enzyme preparation/protease), THERMOASE (trade name) (enzyme preparation/protease), ALCALASE (trade name) (enzyme preparation/protease), PROTIN A (trade name) (enzyme preparation/protease), and the like. It is preferable to use a heat-resistant protease that has a residual activity of about 10% or more when heated at 80° C. for 30 minutes. It is more effective to use a plurality of proteases in combination rather than to use only single protease. The reaction time is preferably about 30 minutes to about 10 hours.

The protease is finally inactivated by heating the reaction solution. The protease may be inactivated by heating the reaction solution at 100° C. or more for 10 seconds or more. After centrifuging the reaction solution, the supernatant liquid is collected, and dried to obtain a powdery product. Since a precipitate that occurs during centrifugation is allergenic as compared with the supernatant liquid, it is preferable to remove such a precipitate. Note that the reaction solution as it is may be dried and sufficiently used. The average peptide length (APL) of the resulting whey protein hydrolysate may be determined by a 2,4,6-trinitrobenzenesulfonate (TNBS) method or the like. The molecular weight distribution of the whey protein hydrolysate may be determined by high-performance size exclusion chromatography (HPSEC) or the like. The free amino acid content in the whey protein hydrolysate may be determined by extracting free amino acids using 75% ethanol or the like, and analyzing the extracted free amino acids using an amino acid analyzer or the like. The hydrolysis rate of the whey protein hydrolysate may be determined by an ortho-phthalaldehyde (OPA) method, in which free amino groups are modified and measured, or the like.

The whey protein hydrolysate of the invention may be used directly as the skin-beautifying agent, or may optionally be used as a preparation incorporated in a powdered preparation, granules, a tablet, a capsule, a drinkable preparation, or the like using a conventional method. A whey protein hydrolysate obtained using an ultrafiltration (UF) membrane or a microfiltration (MF) membrane may also be used directly as the skin-beautifying agent, or may also be used as the skin-beautifying agent after directly drying. The whey protein hydrolysate may also be used as a preparation prepared using a conventional method. The preparation may be added to a nutrient preparation, a food or drink, such as yogurt, milk-based drink, wafer or the like, a nutrient composition, a feed, or a drug.

A skin-beautifying food or drink, a skin-beautifying nutrient composition, a skin-beautifying feed, and a skin-beautifying drug of the invention may include only the whey protein hydrolysate, or may further include raw materials, such as stabilizer, saccharide, lipid, flavor, vitamin, mineral, flavonoid, polyphenol and the like, that are normally contained in a food, drink, feed, or drug, for example. The whey protein hydrolysate may be used in combination with additional ingredients that exhibits a beauty effect, such as sphingomyelin, glucosylceramide, phospholipid and the like, that exhibits a skin-moisturizing effect, and such as collagen, vitamin C, iron and the like that promote skin collagen production, for example. A raw material that is normally contained in a food, drink, or the like may be added to such a skin-beautifying food or drink, skin-beautifying nutrient composition, skin-beautifying feed, or skin-beautifying drug as another raw material.

The content of the whey protein hydrolysate in the skin-beautifying food or drink, the skin-beautifying nutrient composition, the skin-beautifying feed, and the skin-beautifying drug is not particularly limited, but is normally 0.001 to 10% (w/w), and preferably 0.1 to 5% (w/w), based on the total mass of the food or drink, the nutrient composition, the feed, and the drug so that an adult can take the whey protein hydrolysate in an amount of 2 mg/day or more, although the content of the whey protein hydrolysate varies depending on the food or drink, the feed, and the drug. The skin-beautifying cosmetic may be used as a normal cosmetic form such as emulsion, cream, lotion, or pack. Such a cosmetic may be produced by a conventional method, and the whey protein hydrolysate may be appropriately added during the production process. A cosmetic may be produced using such a cosmetic as a raw material. The content of the whey protein hydrolysate in the cosmetic is not particularly limited, but is normally 0.001 to 30% (w/w), and preferably 0.1 to 10% (w/w), based on the total mass of the cosmetic in order to apply the whey protein hydrolysate in an amount of 2 mg/day or more per adult.

A skin-beautifying composition that can be orally or parenterally administered may be prepared by adding an appropriate auxiliary agent to the active ingredient used for the skin-beautifying agent of the invention, and preparing the composition in optional form. When forming the composition, a diluent or vehicle such as a filler, extender, binder, disintegrant, surfactant, lubricant or the like, that is normally added, may be used. Various dosage form of a pharmaceutical preparation may be selective, for example, a capsule, tablet, granules, powder, liquid, suspension, emulsion, suppository, injection, ointment and the like can be given. Examples of the vehicle include sucrose, lactose, starch, crystalline cellulose, mannitol, light anhydrous silicic acid, magnesium aluminate, synthetic aluminum silicate, magnesium aluminometasilicate, calcium carbonate, sodium hydrogen carbonate, calcium hydrogen phosphate, calcium carboxymethyl cellulose, and the like. These compounds may be used either alone or in combination of two or more thereof.

The invention is further described below by way of examples, comparative examples, and test examples. Note that the following examples are intended for illustrative purposes only, and should not be construed as limiting the invention.

Example 1

Papain (50 U/g whey protein) and PROLEATHER (150 U/g whey protein; manufactured by Amano Enzyme Inc.) were added to 1 liter of a 10% whey protein aqueous solution. After adjusting the pH of the mixture to 8, the whey protein was hydrolyzed and denatured at 55° C. for 6 hours. The reaction solution was then heated at 100° C. for 15 seconds or more to inactivate the proteases, and centrifuged. The supernatant liquid was collected, and dried to obtain a whey protein hydrolysate (Example product 1). The whey protein hydrolysate had a molecular weight distribution of 10 kDa or less, a main molecular weight peak of 1.3 kDa, an APL of 7.2, and a free amino acid content of 18.9% (based on the total components). The whey protein hydrolysate had antigenicity equal to or less than 1/10,000th of that of β-lactoglobulin (measured by inhibition ELISA). The hydrolysis rate was 28%, the yield (i.e., the ratio (%) of the dry weight of the supernatant liquid to the dry weight of the raw materials) was 80.3%, and the bitterness was 2. The whey protein hydrolysate thus obtained can be used directly as the skin-beautifying agent according to the invention.

Example 2

Papain (50 U/g whey protein) and PROLEATHER (150 U/g whey protein; manufactured by Amano Enzyme Inc.) were added to 1 l of a 10% whey protein aqueous solution. After adjusting the pH of the mixture to 8, the whey protein was hydrolyzed at 50° C. for 3 hours. The solution was heated to 55° C., and kept the temperature for 3 hours to hydrolyze and denature the whey protein. The mixture was then heated at 100° C. for 15 seconds or more to inactivate the proteases. The reaction solution was filtered using a UF membrane having a molecular weight cut-off of 10 kDa (manufactured by STC) and an MF membrane having a molecular weight cut-off of 300 Da (manufactured by STC) to collect a concentrate fraction. The fraction was dried to obtain a whey protein hydrolysate (Example product 2). The whey protein hydrolysate had a molecular weight distribution of 10 kDa or less, a main molecular weight peak of 500 Da, an APL of 3.0, and a free amino acid content of 15.2% (based on the total components). The whey protein hydrolysate had antigenicity equal to or less than 1/10,000th of that of β-lactoglobulin (measured by inhibition ELISA). The hydrolysis rate thereof was 32%, the yield was 65.4%, and the bitterness was 2. The whey protein hydrolysate thus obtained can be used directly as the skin-beautifying agent according to the invention.

Example 3

120 g of a whey protein was dissolved in 1800 ml of purified water, and the solution was adjusted to pH 7.0 using a 1 M sodium hydroxide solution. The solution was sterilized at 60° C. for 10 minutes, and held at 45° C. After the addition of 20 g of Amano A (manufactured by Amano Enzyme Inc.), the mixture was reacted for 2 hours. After inactivating the protease by heating the mixture at 80° C. for 10 minutes, the mixture was freeze-dried to obtain a whey protein hydrolysate (Example product 3). The hydrolysis rate of the whey protein hydrolysate was 18%, and the yield was 80.6%. The whey protein hydrolysate thus obtained can be used directly as the skin-beautifying agent according to the invention.

Example 4

120 g of a whey protein was dissolved in 1800 ml of purified water, and the solution was adjusted to pH 7.0 using a 1 M sodium hydroxide solution. The solution was sterilized at 60° C. for 10 minutes, and held at 45° C. After the addition of 20 g of Amano A (manufactured by Amano Enzyme Inc.), the mixture was reacted for 8 hours. After inactivating the protease by heating the mixture at 80° C. for 10 minutes, the mixture was freeze-dried to obtain a whey protein hydrolysate (Example product 4). The hydrolysis rate of the whey protein hydrolysate was 25%, and the yield was 80.6%. The whey protein hydrolysate thus obtained can be used directly as the skin-beautifying agent according to the invention.

Comparative Example 1

200 g of casein was suspended in 2000 ml of purified water, and the solution was adjusted to pH 8.0 using a 1 M sodium hydroxide solution and dissolved completely. The solution was sterilized at 80° C. for 10 minutes, and held at 50° C. After the addition of 20 g of Pancreatin F (manufactured by Amano Enzyme Inc.) and 20 g of Amano A (manufactured by Amano Enzyme Inc.), the mixture was reacted for 10 hours. After inactivating the proteases by heating the mixture at 80° C. for 10 minutes, the mixture was freeze-dried to obtain a casein hydrolysate (Comparative example product 1). The hydrolysis rate of the casein hydrolysate was 27%, and the yield was 77.8%.

Comparative Example 2

200 g of casein was suspended in 2000 ml of purified water, and the solution was adjusted to pH 8.0 using a 1 M sodium hydroxide solution and dissolved completely. The solution was sterilized at 80° C. for 10 minutes, and held at 40° C. After the addition of 15 g of Pancreatin F (manufactured by Amano Enzyme Inc.), the mixture was reacted for 5 hours. After inactivating the protease by heating the mixture at 80° C. for 10 minutes, the mixture was freeze-dried to obtain a casein hydrolysate (Comparative example product 2). The hydrolysis rate of the resulting casein hydrolysate was 20%, and the yield was 79.1%.

Test Example 1

Animal Experiment

A skin-moisturizing effect was evaluated using whey protein hydrolysates of Example products 1, 3, and 4 and casein hydrolysates of Comparative example products 1 and 2. 13-week-old hairless mice (Hos: HR-1) were used for the experiment. The mice were divided into following eight groups (8 mice/group); a group to which physiological saline was administered (Group A), a group to which whey protein hydrolysate of Example product 1 was administered in an amount of 2 mg/kg weight (Group B), a group to which whey protein hydrolysate of Example product 1 was administered in an amount of 5 mg/kg weight (Group C), a group to which whey protein hydrolysate of Example product 1 was administered in an amount of 10 mg/kg weight (Group D), a group to which whey protein hydrolysate of Example product 3 was administered in an amount of 10 mg/kg weight (Group E), a group to which whey protein hydrolysate of Example product 4 was administered in an amount of 10 mg/kg weight (Group F), a group to which casein hydrolysate of Comparative example product 1 was administered in an amount of 10 mg/kg weight (Group G), and a group to which casein hydrolysate of Comparative example product 2 was administered in an amount of 10 mg/kg weight (Group H). Each mouse was orally administered once a day using a sonde, and kept for 3 weeks. Example products 1, 3, and 4 and Comparative example products 1 and 2 were suspended in physiological saline, and orally administered to the Groups B to H. The moisture content in the tail of each mouse and the transepidermal water loss from the tail of each mouse were measured at the beginning and the end of the test, and the values (the moisture content and the transepidermal water loss) at the end of the test were calculated as a ratio (increase ratio) with respect to the values at the beginning of the test which were assumed 100. The moisture content in the skin and the transepidermal water loss were respectively measured using a Corneometer and a Tewameter (manufactured by Courage & Khazaka). The results are shown in Table 1.

TABLE 1

| Group | Moisture content increase ratio (%) | Transepidermal water loss increase ratio (%) |
| --- | --- | --- |
| Group A | 89 | 103 |
| Group B | 124 | 86 |
| Group C | 148 | 83 |
| Group D | 153 | 80 |
| Group E | 117 | 90 |
| Group F | 122 | 88 |
| Group G | 98 | 101 |
| Group H | 99 | 99 |

As shown in Table 1, while Group A showed that the moisture content decreased after 3 weeks of administration, Group B showed that the moisture content increased about 1.25 times after 3 weeks of administration, and Groups C and D showed that the moisture content increased up to about 1.5 times after 3 weeks of administration. Groups E and F showed that the moisture content increased up to about 1.2 times after 3 weeks of administration. In contrast, in the cases of the groups to which casein hydrolysate of Comparative example product 1 or 2 was administered, both the moisture content and transepidermal water loss did not change between the beginning and end of the test. It was confirmed from these results that the whey protein hydrolysate according to the invention exhibited a skin-moisturizing effect. It was also confirmed that the skin-moisturizing effect was achieved when the whey protein hydrolysate was administered in an amount of at least 2 mg/kg weight.

Test Example 2

Animal Experiment

A collagen production-promoting effect was evaluated using whey protein hydrolysate of Example product 2 and casein hydrolysates of Comparative example products 1 and 2. 7-week-old Wistar male rats were divided into following six groups (6 mice/group); a group to which physiological saline was administered (Group A), a group to which whey protein hydrolysate of Example product 2 was administered in an amount of 2 mg/kg weight (Group B), a group to which whey protein hydrolysate of Example product 2 was administered in an amount of 5 mg/kg weight (Group C), a group to which whey protein hydrolysate of Example product 2 was administered in an amount of 10 mg/kg weight (Group D), a group to which casein hydrolysate of Comparative example product 1 was administered in an amount of 10 mg/kg weight (Group E), and a group to which casein hydrolysate of Comparative example product 2 was administered in an amount of 10 mg/kg weight (Group F). Each rat was administered once a day using a sonde, and kept for 10 weeks. Example product 2 and Comparative example products 1 and 2 were suspended in physiological saline, and orally administered to Groups B to F. The amount of collagen in the skin was determined by treating the derma of each rat in accordance with the method of Nimni et al. (see Arch. Biochem. Biophys., p. 292, 1967), and measuring the hydroxyproline content in the soluble fraction. Hydroxyproline is a special amino acid that is contained only in collagen, and accounts for about 10% of the amino acids that form collagen. Therefore, the amount of collagen can be estimated by measuring the hydroxyproline content (see Asano Ryuji et al., BioIndustry, p. 12, 2001). The results are shown in Table 2.

TABLE 2

| Hydroxyproline content (μg/ml) | |
|---|---|
| Group A | 0.3 ± 0.1 |
| Group B | 0.9 ± 0.2* |
| Group C | 1.3 ± 0.3* |
| Group D | 1.4 ± 0.3* |
| Group E | 0.5 ± 0.2 |
| Group F | 0.4 ± 0.1 |

The values shown in Table 2 indicate "mean ± standard deviation" (n = 6).
The symbol "*" indicates that there was a significant difference as compared with Group A (control group) ($p < 0.05$).

As shown in Table 2, the amount of hydroxyproline in the soluble fraction after 10 weeks of administration was significantly larger in Groups B, C, and D as compared with Group A. Groups E and F did not show a difference in the amount of hydroxyproline in the soluble fraction after 10 weeks of administration from Group A. It was confirmed from these results that the whey protein hydrolysate according to the invention exhibited a skin collagen production-promoting effect. It was also confirmed that the skin collagen production-promoting effect was achieved when the whey protein hydrolysate was administered in an amount of at least 2 mg/kg weight.

Example 5

Preparation of Skin-Beautifying Cosmetic (Lotion)

A lotion-type skin-beautifying cosmetic (Example product 5) was prepared by mixing the raw materials in the composition shown in Table 3.

TABLE 3

| Sorbitol | 3.0 |
|---|---|
| Sodium DL-pyrrolidone carboxylate | 2.0 |
| Carboxymethyl cellulose | 0.3 |
| Parabene | 0.1 |
| Example product 2 | 0.05 |
| Flavor | Proper quantity |
| Sterilized ion-exchanged water | Balance (total: 100) |

Example 6

Preparation of Skin-Beautifying Cosmetic (Cream)

A cream-type skin-beautifying cosmetic (Example product 6) was prepared by mixing the raw materials in the composition shown in Table 4.

TABLE 4

| Glycerol monostearate (self-emulsifiable) | 10.0 |
|---|---|
| Purified lanolin | 6.0 |
| Liquid paraffin | 5.0 |
| Jojoba oil | 5.0 |
| Parabene | 0.3 |
| Example product 1 | 0.5 |
| Flavor | Proper quantity |
| Sterilized ion-exchanged water | Balance (total: 100) |

Test Example 3

A clinical test was performed using Example product 5 and Example product 6. A comparative lotion and a comparative cream were produced in the same manner as Example product 5 or Example product 6, except that the whey protein hydrolysate was not added. Twenty adult females having face with dry skin, slacks and fine wrinkles of the skin were divided at random into two groups each having 10 subjects (Groups A and B), and twenty adult females having hands and fingers with rough skin were divided at random into two groups each having 10 subjects (Groups C and D). 2 g of Example product 5, 2 g of the comparative lotion, 2 g of Example product 6, and 2 g of the comparative cream were applied to the faces of Group A, the faces of Group B, the hands and fingers of Group C, and the hands and fingers of Group D, respectively, in the same way as usual twice a day for 10 days. The results are shown in Table 5.

TABLE 5

| | Dry feeling | Rough skin | Wrinkles | Slacks |
|---|---|---|---|---|
| Group A | ++ | ++ | ++ | + |
| Group B | ± | ± | ± | ± |
| Group C | + | + | Not measured | Not measured |

TABLE 5-continued

| | Dry feeling | Rough skin | Wrinkles | Slacks |
|---|---|---|---|---|
| Group D | ± | ± | Not measured | Not measured |

++; A significant effect was observed after 10 days of application
+; A effect was observed after 10 days of application
±; Any effect was not observed after 10 days of application (same as ten days before)

As shown in Table 5, it was confirmed that Example product 5 significantly improved skin dry feeling, rough skin and the like, and exhibited a skin-beautifying effect as compared with the comparative lotion. It was also confirmed that Example product 6 significantly improved skin dry feeling, rough skin, and suppressed spontaneous exacerbation, such as rough skin or the like as compared with the comparative cream.

Example 7

Preparation of Skin-Beautifying Tablet

The raw materials were mixed in the composition shown in Table 6. 1 g of the resulting mixture was formed and tableted by a conventional method to obtain a skin-beautifying tablet according to the invention. 1 g of the skin-beautifying tablet contained whey protein hydrolysate of Example product 1 in an amount of 50 mg.

TABLE 6

| Hydrous crystalline glucose | 88.5 (wt %) |
|---|---|
| Mineral mixture | 5.0 |
| Example product 1 | 5.0 |
| Sugar ester | 1.0 |
| Flavor | 0.5 |

Example 8

Preparation of Skin-Beautifying Liquid Nutrient Composition 50 g of whey the protein hydrolysate of Example product 2 was dissolved in 4950 g of deionized water. The solution was heated to 50° C., and mixed with stirring at 6000 rpm for 30 minutes using a TK-homomixer ("TK ROBOMICS" manufactured by PRIMIX Corporation) to obtain a whey protein hydrolysate solution which contained the whey protein hydrolysate of Example product 2 in an amount 50 g/5 kg. 5.0 kg of casein, 5.0 kg of soybean protein, 1.0 kg of fish oil, 3.0 kg of perilla oil, 17.0 kg of dextrin, 6.0 kg of mineral mixture, 1.95 kg of vitamin mixture, 2.0 kg of emulsifier, 4.0 kg of stabilizer, and 0.05 kg of flavor were added to 5.0 kg of the whey protein hydrolysate solution. The resulting mixture was charged in a 200 ml retort pouch. The mixture was then sterilized at 121° C. for 20 minutes using a retort sterilizer (class-1 pressure vessel, "RCS-4CRTGN" manufactured by Hisaka Works, Ltd.) to obtain 50 kg of a skin-beautifying liquid nutrient composition according to the invention. The skin-beautifying liquid nutrient composition contained the whey protein hydrolysate of Example product 2 in an amount of 100 mg/100 g.

Example 9

Preparation of Skin-Beautifying Drink 300 g of a skim milk powder was dissolved in 409 g of deionized water, and 1 g of the whey protein hydrolysate of Example product 1 was dissolved in the solution. The solution was heated to 50° C., and mixed with stirring at 9500 rpm for 30 minutes using an ultra-disperser ("ULTRA-TURRAX T-25" manufactured by IKA Japan). After the addition of 100 g of maltitol, 2 g of acidifier, 20 g of reduced starch syrup, 2 g of flavor, and 166 g of deionized water, the resulting mixture was charged in a 100 ml glass bottle. After sterilizing the mixture at 95° C. for 15 minutes, the bottle was closely sealed, thereby 10 bottles (100 ml each) of a skin-beautifying drink of the invention were prepared. The skin-beautifying drink contained the whey protein hydrolysate of Example product 1 in an amount of 100 mg/100 ml.

Example 10

Preparation of Skin-Beautifying Dog Food 2 kg of the whey protein hydrolysate of Example product 2 was dissolved in 98 kg of deionized water. The solution was heated to 50° C., and mixed for stirring at 3600 rpm for 40 minutes using a TK-homomixer ("MARK II 160" manufactured by PRIMIX Corporation) to obtain a whey protein hydrolysate solution which contained the whey protein hydrolysate of Example product 2 in an amount of 2 g/100 g. 12 kg of soybean meal, 14 kg of powdered skim milk, 4 kg of soybean oil, 2 kg of corn oil, 23.2 kg of palm oil, 14 kg of corn starch, 9 kg of flour, 2 kg of bran, 5 kg of vitamin mixture, 2.8 kg of cellulose and 2 kg of mineral mixture were added to 10 kg of the whey protein hydrolysate solution. The mixture was sterilized at 120° C. for 4 minutes to obtain 100 kg of a skin-beautifying dog food according to the invention. The skin-beautifying dog food contained the whey protein hydrolysate of Example product 2 in an amount of 200 mg/100 g.

The invention claimed is:

1. A method of treating dry skin, comprising applying whey protein hydrolysate to the skin of a person who has dry skin, wherein the whey protein hydrolysate is obtained by exposing a whey protein to a heat-resistant protease at a temperature of 45 to 70° C. and has a free amino acid content of 20% or less by weight based on the total components of the hydrolysate.

2. The method according to claim 1, wherein the whey protein hydrolysate is present in a cosmetic.

3. The method according to claim 2, wherein the cosmetic is in the form of an emulsion, cream, lotion or pack.

4. The method according to claim 2, wherein:
the molecular weight of the whey protein hydrolysate is 10 kDa or less and the main molecular weight peak thereof is 200 Da to 3 kDa;
the average peptide length of the whey protein hydrolysate is 2 to 8; and
the antigenicity of the whey protein hydrolysate is equal to or less than 1/10,000th of that of β-lactoglobulin.

5. The method according to claim 1, wherein:
the molecular weight of the whey protein hydrolysate is 10 kDa or less and the main molecular weight peak thereof is 200 Da to 3 kDa;
the average peptide length of the whey protein hydrolysate is 2 to 8; and
the antigenicity of the whey protein hydrolysate is equal to or less than 1/10,000th of that of β-lactoglobulin.

6. A method of moisturizing or protecting mammalian skin, comprising applying whey protein hydrolysate to the skin of a mammal with dry skin, wherein the whey protein hydrolysate is obtained by exposing a whey protein to a heat-resistant protease at a temperature of 45 to 70° C. and has a free amino acid content of 20% or less by weight based on the total components of the hydrolysate.

7. A method of moisturizing or protecting mammalian skin, comprising applying a cosmetic in the form of an emulsion, cream, lotion, or pack and comprising a whey protein hydrolysate obtained by exposing a whey protein to a heat-resistant protease at a temperature of 45 to 70° C.,
   wherein the whey protein hydrolysate has the following characteristics (A) to (D):
   (A) the molecular weight thereof is 10 kDa or less and the main molecular weight peak thereof is 200 Da to 3 kDa,
   (B) the average peptide length thereof is 2 to 8,
   (C) the free amino acid content thereof is 20% or less by weight based on the total components of the hydrolysate, and
   (D) the antigenicity thereof is equal to or less than 1/10,000th of that of β-lactoglobulin, to the skin of a mammal having dry skin.

* * * * *